United States Patent
Waldbillig

[11] 3,940,409
[45] Feb. 24, 1976

[54] ALKYLIDENIMINO THIADIAZOLE CONTAINING MIXTURE

[75] Inventor: James O. Waldbillig, Wappingers Falls, N.Y.

[73] Assignee: Texaco Inc., New York, N.Y.

[22] Filed: Sept. 9, 1974

[21] Appl. No.: 504,637

Related U.S. Application Data

[62] Division of Ser. No. 445,385, Feb. 25, 1974, Pat. No. 3,865,739.

[52] U.S. Cl. .......................................... 260/306.8 D
[51] Int. Cl.$^2$ ..................................... C07D 285/12
[58] Field of Search ................ 260/306.8 D, 302.5 D

[56] References Cited
UNITED STATES PATENTS
2,898,342   8/1959   Avakian et al. ............... 260/306.8 D

*Primary Examiner*—Richard J. Gallagher
*Attorney, Agent, or Firm*—T. H. Whaley; C. G. Ries

[57] ABSTRACT

Thiadiazole derivative mixture containing as a principal component a product characterized by the formula

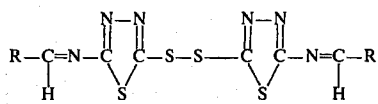

where R is alkyl of from 2 to 30 carbons prepared by the method consisting of first contacting 2-amino-5-mercapto-1,3,4-thiadiazole with an alkanal of the formula RCHO where R is a heretofore defined and second contacting the resultant reaction mixture with dimethyl sulfoxide. Lubricating oil composition comprising a hydrocarbon oil of lubricating viscosity containing between about 0.01 and 50 wt. % of said thiadiazole derivative mixture.

2 Claims, No Drawings

ALKYLIDENIMINO THIADIAZOLE CONTAINING MIXTURE

This is a division of application Ser. No. 445,385 filed Feb. 25, 1974, now U.S. Pat. No. 3,865,739.

BACKGROUND OF INVENTION

In the internal combustion engines of today as well as the mechanisms associated therewith such as automatic transmissions, a substantial amount of copper is employed in the construction thereof. However, some of the most commonly used additives in lubricating oil compositions servicing the internal combustion systems, e.g., gear oils (automatic transmission fluid) contain compounds which are highly corrosive to copper. Specifically, among the more effective agents which have been developed for compounding with lubricants to improve extreme pressure and wear properties are sulfur containing organic compounds, for example, sulfurized triisobutylene, sulfurized diisobutylene, sulfurized terpene, sulfurized hydrocarbon oils, vegetable oils, animal oils, xanthate esters, organic polysulfides, particularly polyalkyl polysulfides which contain active sulfur or sulfur compounds which are corrosive to copper. In addition, those hydrocarbon oils derived from high sulfur containing crude oils wherein the sulfurous compounds are not thoroughly removed in refining are often corrosive to copper elements in automotive systems.

To solve this problem of copper corrosion, the prior art has employed various copper corrosion inhibitors with a varying degree of effectiveness. One class of such inhibitors are disclosed in U.S. Pat. Nos. 2,719,125 and 2,719,126 which are directed to copper corrosion inhibited lubricating oil compositions containing as the copper corrosion inhibitor a 1,3,4-thiadiazole polysulfide characterized by the formula:

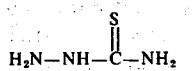

where $R^1$ is a hydrocarbon radical such as alkyl of from 1 to 30 carbons and $x$ is an integer of from 0 to 8. It is interesting to note that the fact that this particular sulfurous material is an effective copper corrosion inhibitor whereas the aforementioned sulfur containing anti-wear and extreme pressure additives are corrosive to copper. This indicates unpredictability regarding the function of sulfur compounds as copper corrosion inhibiting agents.

SUMMARY OF INVENTION

I have discovered and this constitutes one aspect of my invention, a novel thiadiazole derivative mixture which is effective in inhibiting the corrosion of copper by hydrocarbon oil formulations of lubricating viscosity. More particularly, the instant invention relates to a mixture containing as a principal product alkylidenimino thiadiazole product characterized by the formula:

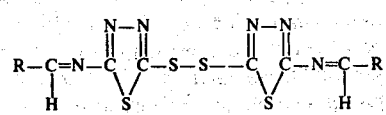

where R is alkyl of from 2 to 30 carbons prepared by first contacting 2-amino-5-mercapto-1,3,4-thiadiazole with an alkanol of the formula RCHO and second contacting the resultant reaction mixture with dimethylsulfoxide. The invention also pertains to hydrocarbon oil concentrates and finished hydrocarbon oil compositions thereof comprising a hydocarbon oil of lubricating viscosity and said alkylidenimino thiadiazole containing mixture.

DETAILED DESCRIPTION OF THE INVENTION

Specifically, the alkylidenimino thiadiazole containing mixture is prepared by first reacting thiosemicarbazide of the formula:

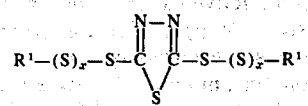

with carbon disulfide to form 2-amino-5-mercapto-1,3,4-thiadiazole. The reaction is carried out at a temperature between about 20° and 200°C. utilizing a mole ratio of thiosemicarbazide to carbon disulfide of between about 1:10 and 2:1 advantageously in the presence of a solvent such as N,N-dimethylformamide, N,N-diethylformamide, N-methyl-N-ethylformamide, N,N-dimethylacetamide, N,N-diethylacetamide, N-methyl-N-ehtylacetamide, N-formyl piperidine. Further description of the 2-amino-5-mercapto-1,3,4-thiadiazole can be found in U.S. Pat. No. 2,389,126.

The formed 2-amino-5-mercapto-1,3,4-thiadiazole is then contacted with an alkanal characterized by the formula RCHO where R is alkyl of from 2 to 30 carbons at a temperature between about 20° and 250°C. utilizing a mole ratio of thiadiazole reactant to aldehyde of between about 10:1 and 1:2 to form an intermediate product of the Schiff base type characterized by the formula:

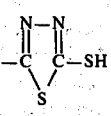

where R is as heretofore defined. This reaction step is carried out in a liquid diluent such as benzene, toluene, o, m, or p-xylene and mixtures thereof, chlorobenzene, o, m, or p-dichlorobenzene and mixtures thereof, $C_5$ to $C_{30}$ alkanes and mixtures thereof, or a mineral oil, preferably at reflux in benzene or a mixture of benzene and dimethylformamide.

In the final phase of the method the formed Schiff base intermediate product is contacted with dimethyl sulfoxide at a temperature between about 20° and 150°C. utilizing a mole ratio of said intermediate to dimethyl sulfoxide of between about 3:1 and 1:50 to form the thiadiazole derivative mixture containing as a principal product an alkylidenimino thiadiazole characterized by the formula:

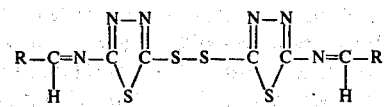

where R is as heretofore defined. This reaction phase is preferably conducted in the presence of a liquid diluent such as benzene, toluene, o, m, or p-xylene and mixtures thereof, chlorobenzene, o, m, or p-dichlorobenzene and mixtures thereof, $C_5$ to $C_{30}$ alkanes and mixtures thereof, or a mineral oil.

Under preferred conditions, the reaction is carried out at reflux in benzene or benzene dimethylformamide solution. If desired, the products of each stage can be isolated by standard means such as removing diluent as overhead at elevated tempeatures under reduced pressure leaving the product as residue. If a more purified product mixture is desired, standard purification techniques may be employed such as recrystallization.

Examples of the alkanal reactant contemplated in the second stage are lauryldehyde, propionaldehyde, butyroldehyde, valeraldehyde, hexanal heptaldehyde, octylaldehyde, 2-ethylhexanol nonyl aldehyde, decyl aldehyde, undecylic aldehyde, myristyl aldehyde, octadecyl aldehyde, citronellal, and citral aldehydes of 20 or more carbons are preferred.

Characterized examples of the Schiff base intermediate product and the alkylidenimino thiadiazole final product are

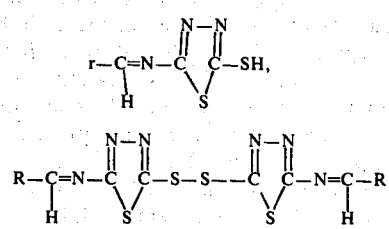

where R is undecyl, ethyl, propyl, butyl, pentyl, hexyl, heptyl, 2-heptyl, octyl, nonyl, decyl, tridecyl, heptadeyl; 2,6-dimethyl-1,5-heptadienyl or 2,6-dimethyl-5-heptenyl.

It is to be noted the thiadiazole derivative mixture product of the invention is a complex mixture of many compounds which vary in nature and quantities depending on the particular process ingredients, conditions and quantities. As heretofore stated, the mixture does contain as a principal product an alkylidenimino thiadiazole. Other compounds presumedly present are telomers, thioketals,

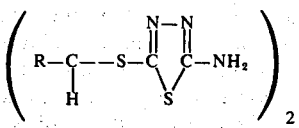

where R is as heretofore defined, etc. Accordingly, definition of the product mixture requires that it be at least in part characterized in terms of process.

In regad to the finished compositions of the present invention, the alkylidenimino thiadiazole containing mixtures are employed in a hydrocarbon base oil in copper corrosion inhibiting amounts, namely, from between about 0.01 and 10 wt. %, preferably between about 0.05 and 10 wt. %. The hydrocarbon base oil normally constitutes at least about 85 wt. % of the finished composition, preferably about 90 wt. % or more. By the term "finished" it is intended to denote that the composition is in condition for ultimate use without need for further dilution with base oil.

In the concentrate compositions contemplated herein to which additional hydrocarbon oil is added to from finished compositions, the concentrate form being preferably for storage and transport, the hydrocarbon base oil normally constitutes at least about 50 wt. % and the alkylidenimino thiadiazole product containing mixture about 10 and 50 wt. % of the concentrate formulation.

Thus, compositions are contemplated ranging from at least about 50 wt. % hydrocarbon oil and between about 0.01 and 50 wt. % of the alkylidenimino thiadiazole containing mixture.

The hydrocarbon oil components employed in the finished and concentrate formulations of the invention advantageously are mineral lubricating oils such as paraffinic lube oil, naphthenic lube oil and mixtures thereof. Other suitable hydrocarbon oils ar those synthetically formed such as the polyalkylenes, e.g., polyisobutylene of molecular weights of from 1000 to 5000. The viscosity of the base oils employed will be dependent upon the particular use intended for the finished formulation and will generally range between about 70 and 5000 SUS at 100°F.

In addition to the hydrocarbon oil and thiadiazole derivative mixture components in the oil compositions of the invention, additional additives are normally employed, the particular additives utilized being dependent upon the specific use intended for the finished compositions of the invention. Some of the additional additives contemplated belong in the classes of detergent-dispersants, pour depressants, VI improvers, extreme pressure agents, antiwear agents, antioxidants, antifoamants supplementary corrosion inhibitors.

Examples of the extreme pressure agents and antiwear agents are dithiolethione derived from sulfurizing triisobutylene and alkyl sulfides, disulfides and polysulfides prepared by sulfurization of isobutylene with sulfur chloride. Other extreme pressure and antiwear agents contemplated are the sulfurized terpenes, sulfurized hydrocarbon oils and polyalkyl polysulfides, all of which contain active sulfur or sulfur compounds which are corrosive to copper. These extreme pressure and antiwear agents are normally present in the finished formulations in amounts of between about 0.1 and 10 wt. %, preferably between 0.5 and 5 wt. %.

When detergent-dispersants are employed, they are usually utilized in amounts between about 0.5 and 5 wt. %. Examples of ashless dispersants are the alkenyl succinimides characterized by the general formula:

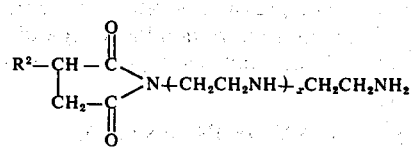

where $R^2$ is monoolefinic aliphatic hydrocarbon radical of from about 50 to 200 carbons and $x$ is an integer of from 1 to 10 derived from a polyethylene polyamine. Particularly suitable derivatives are the diethylene triamine, ditriethylene tetramine, tetraethylene pentamine of polyisobutylene succinic anhydride, particularly where $R^2$ is of a molecular weight between about 700 and 2000, e.g., about 1300. These ashless dispersants are further described in U.S. Pat. No. 3,172,892 and 3,202,678. The non ashless dispersants that may be utilized are the alkaline earth metal overbased calcium alkaryl sulfonates such as carbon dioxide overbased calcium alkaryl sulfonate wherein the alkaryl sulfonate moiety is of a molecular weight of 500 to 1000. The overbased sulfonates are further described in U.S. Pat. Nos. 3,027,325, 3,312,618 and 3,537,996.

Examples of contemplated viscosity index improvers which in many instances function as pour depressors are the methacrylate ester polymers characterized by the general formula:

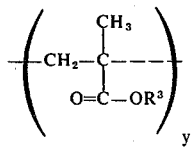

where $R^3$ is alkyl, dialkylaminoalkyl (e.g. dimethylaminoethyl) or a mixture of such groups containing from 1 to 20 carbons and y is an integer providing a molecular weight of the polymer in the range of 25,000 to 1,250,000, preferably 50,000 to 500,000. Methacrylate ester polymers possessing pour depressant as well as viscosity index improving properties are well known, e.g., U.S. Pat. No. 2,737,496. A very effective material of this type is the tetrapolymer of butyl, lauryl, stearyl and dimethylaminoethyl methacrylate in approximate ratios of 1:2:1:0.2. The methacrylate ester is advantageously employed in the base oil in an amount ranging from about 0.1 to 10 wt. %, preferably about 0.2 to 5 wt. %, in order to impart the desired viscosity index and/or pour point.

Examples of suitable antioxidants which also function as supplementary corrosion inhibitors are the aryl substituted amine compound exemplified by phenylnaphthyl amine as well as compounds such as phenylene diamine, phenathiazine, diphenylamines employed in amounts between about 0.1 and 5 wt. %. Particularly preferred compounds are the phenylalpha-naphthyl amines and a mixture of 2,2-diethyl-4,4′-tdioctyldioctyldiphenylamine and 2,2′-diethyl-4,4,6-octyldiphenylamine.

Additional examples of antioxidants are the hydrocarbyl dithiophosphates, particulaly effective compounds in this class are zinc di(nonylphenoxyethyl) dithiophosphate, zinc di(dodecylphenoxyethyl) dithiophosphate and zinc di(nonylphenoxyethoxyethyl) dithiophosphate prepared by reacting nonyl phenol-ethylene oxide compounds with phosphorus pentasulfide followed by neutralization of the acid formed with a basic zinc compound such as zinc carbonate, zinc oxide or zinc hydroxide. The general preparation and description of the compounds in this class are disclosed in U.S. Pat. Nos. 2,344,395 and 3,293,181.

Supplemental corrosion inhibitor examples are oleylamine and ethyloleyl acid phosphate, and mixtures of mercaptobenzothiazoles and alkyl amines.

Antifoamants which are suitable for use are the silicone polymers such as dimethyl silicone polymer.

The following examples further illustrate the invention but are not to be construed as limitations thereof.

EXAMPLE I

This example illustrates the preparation of the 2-mercapto-5-amino-1,3,4-thiadiazole precursor.

To a solution of 18.2 grams (0.02 mole) of thiosemicarbazide in 200 grams of dimethylformamide there was charged 16.8 grams (0.2 mole) of carbon disulfide. The resultant mixture was heated to and maintained at 50°C. for a period of 4 hours. The reaction mixture was then stripped on a rotary evaporator leaving a solid residue. The solid was dissolved in 500 mls. of anhydrous ethanol and 2 grams of the product crystallized from the ethanol and was analyzed and identified as 2-mercapto-5-amino-1,3,4-thiadiazole of the following analysis: Calc. 31.5 (actual 36.2) wt. % nitrogen, 48.1 (44.5) wt. % sulfur, 18 (20.2) wt. % carbon and 2.3 (3.7) wt. % hydrogen.

EXAMPLE II

This example further illustrates the preparation of the 2-mercapto-5-amino-1,3,4-thiadiazole starting reactant.

To a solution of 9.1 grams (0.1 mole) of thiosemicarbazide in 200 mls. of dimethylformamide there was charged 8.4 grams (0.11 mole) of carbon disulfide. The resultant solution was heated for 4 hours at 80°C. The product was then stripped to 200°F. at 0.15 mm Hg. The residue was stirred with 500 mls. of benzene and after removal of the benzene the product was redissolved in 500 mls. of hot ethanol. Seven grams of the product were recovered upon cooling and analyzed. It was determined to be 2-mercapto-5-amino-1,3,4-thiadiazole of the following analysis: Calc. 31.6 (32.4) wt. % nitrogen 48.1 (46.3) wt. % sulfur, 18 (17.9) wt. % carbon and 2.3 (2.6) wt. % hydrogen.

EXAMPLE III

This example still further illustrates the preparation of 2-amino-5-mercapto-1,3,4-thiadiazole starting reactant.

To a solution of 45.5 (0.5 mole) of thiosemicarbazide in 1000 mls. of dimethylformamide there was charge 32 grams of carbon disulfide. The resultant solution was heated for 4 hours at 80°C. and then stripped to 200°F. under a reduced pressure at 0.15 mm Hg. The residue was slurried with 250 mls. of benzene followed by the removal of the benzene via distillation. The residue product was recrystallized from 2500 mls. of Formula 30 to yield 28 grams (42 wt. % yield) which was analyzed and found to be 2-amino-5-mercapto-1,3,4-thiadiazole having an elemental analysis of Calc. 31.6 (31.7) wt. % nitrogen, 48.1 (47.1) wt. % sulfur, 18 (19.2) wt. % carbon and 2.3 (2.1) wt. % hydrogen.

EXAMPLE IV

This example illustrates the preparation of the thiadiazole derivative product mixture of the invention.

A mixture of 9.2 grams (0.05 mole) lauraldehyde, 6.65 grams (0.05 mole) 2-mercapto-5-amino-1,3,4-thiadiazole of the type prepared in Example III and 200 mls. of benzene were heated to reflux (80°C.) to remove as overhead 0.4 mls. of insoluble phase. To the residual refluxed mixture 3 mls. of dimethylsulfoxide were added and the formed mixture was again heated at reflux to remove 0.2 mls. water (theory 0.45 mls.) as overhead. The product was then stripped to 93°C. under reduced pressure (0.175 mm Hg). The residue was identified as a derivative mixture containing as a principal product aluraldehyde reaction product of 2-mercapto-5-amino-1,3,4-thiadiazole characterized by the formula:

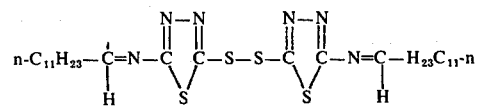

Elemental mixture analysis gave Calc. 14.1 (14.0) wt. % nitrogen and 21.5 (22.4) wt. % sulfur.

EXAMPLE V

This example further illustrates the preparation of the thiadiazole derivative product mixture of the invention.

To a mixture of 6.65 grams (0.05 mole) of 2-amino-5-mercapto-1,3,4-thiadiazole prepared in Example III and 200 mls. of benzene there was charged 9.2 grams (0.05 mole) of lauraldehyde. The resultant mixture was heated to reflux (80°C.) to remove 0.2 mls. of insoluble phase as overhead. To the refluxed mixture there was charged 50 mls. of dimethylformamide and the resultant mixture was again refluxed with 1 ml. of insoluble phase removed as overhead. After cooling of the mixture, the dimethyl sulfoxide in an amount of 50 mls. was added and 0.2 mls. of water (0.9 mls. theory) was removed as azeotrope. The product was stripped to 93°C. and the resultant residue was identified as a derivative mixture containing as a principal product the lauraldehyde reaction product of 2-mercapto-5-amino-1,3,4-thiadiazole characterized by the formula:

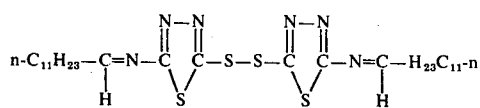

The elemental mixture analysis gave Calc. 14.1 (13.3) wt. % nitrogen and 21.5 (20.5) wt. % sulfur.

EXAMPLE VI

This example illustrates the lubricating oil composition and the effectiveness of the alkylamino thiadiazole dimer component as a copper corrosion inhibitor.

The following is a description of the base oil formulation to which the thiadiazole derivative product mixture producted in Example I was added in varying amounts and to which comparative inhibitor components were added, the resultant formulations being subjected to the ASTM Copper Strip Corrosion Test (D 130-56). Briefly, this test comprises placing a polished copper strip in the test oil composition for a 3 hour period at 250°F. whereupon the degree of corrosive attack on the strip is measured in a rating ranging from 1A to 4C with the rating of 1A representing the least corrosive attack and the rating of 4C represents the greatest corrosive attack.

The following Table I is a description of the base oil formulation:

TABLE I

| Ingredients | Wt. % Base Oil A | Wt. % Base Oil B |
| --- | --- | --- |
| Paraffinic Oil (1000 SUS at 100°F.) | 93.1 | 95 |
| Ethyloleyl Acid Phosphate | 1.0 | — |
| Sodium Sulfide Treated Diisobutylene Polysulfide* | 5.0 | 5 |
| Terpolymer of butyl, lauryl, stearyl and dimethyl aminoethyl methacrylates | 0.2 | — |
| Mixture of 2-mercaptobenzothiazole and t-$C_{18}$-$C_{22}$ alkylamine | 0.5 | — |
| Oleylamine | 0.2 | — |
| Dimethyl Silicone Antifoamant | 100 ppm | — |

*An extreme pressure agent but corrosive to copper.

Table II below contains a description of the representative formulations of the invention, comparative formulations and their effectiveness in inhibiting the corrosion of copper basis the ASTM Copper Strip Corrosion Test.

TABLE II

| Run No. | Base Oil | Test Formulation And Copper Inibitor Properties Cu Corrosion Inhibitor | Inhibitor Conc.Wt.% | Cu Strip Rating |
| --- | --- | --- | --- | --- |
| 1 | A | Ex.IV Prod. | 0.05 | 2A |
| 2 | A | Ex.IV Prod. | 0.10 | 1B |
| 3 | A | Ex.IV Prod. | 0.20 | 2B |
| 4 | B | Ex.IV Prod. | 0.10 | 2B |
| 5 | A | None | 0 | 4A |
| 6 | B | None | 0 | 4A |
| 7 | A | 2,5-bis-(t-octyldithio) 1,3,4-thiadiazole* | 0.1 | 1B |
| 8 | B | same* | 0.1 | 4A |

*Well known commercial copper corrosion inhibitor for gear oils.

In above Table II a comparison of the copper strip rating of representative Run Nos. 1-4 utilizing the dimer product of the invention with the copper strip ratings of comparative Run Nos. 5 and 6 wherein no derivative product mixture of the invention is employed demonstrates the outstanding effectiveness of the dimer product and compositions containing same as a copper corrosion inhibitor. Further, comparison of the copper rating of representative Run No. 4 with comparative Run No. 8 where in the latter run the derivative product of the invention is substituted with a well known copper corrosion inhibitor, shows that the mixtures of the invention are substantially more effective copper corrosion inhibitors than the prior art inhibitors, particularly a comparison of the data relating to the Base Oil B formulations.

I claim:

1. A thiadiazole derivative mixture containing as a principal product an alkylidenimino thiadiazole characterized by the formula:

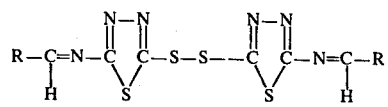

where R is alkyl of from 2 to 30 carbons, said mixture prepared by the process consisting essentially of first contacting 2-amino-5-mercapto-1,3,4-thiadiazole with an alkanal of the formula RCHO where R is alkyl of from 2 to 30 carbons at a temperature of between about 20 and 250°C. tuilizing a mole ratio of 2-amino-5-mercapto-1,3,4-thiadiazole to alkanal of between about 10:1 and 1:2 to form an intermediate thiadiazole product characterized by the formula:

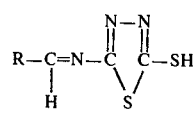

and second contacting said thiadiazole intermediate with dimethyl sulfoxide at a temperatue of between about 20 and 150°C. utilizing a mole ratio of said intermediate to said dimethyl sulfoxide of between about 3:1 and 1:50 to form said thiadiazole derivative mixture, said first and second contacting conducted in the presence of a liquid solvent.

2. A mixture in accordance with claim 1 wherein R is undecyl and said alkanal is lauraldehyde.

* * * * *